(12) United States Patent
Xu

(10) Patent No.: US 7,867,979 B2
(45) Date of Patent: Jan. 11, 2011

(54) DRUG COMPOSITION FOR TREATING 2 TYPE DIABETES AND DIABETIC CHRONICITY COMPLICATIONS

(75) Inventor: Guang'ai Xu, Haikou Hainan (CN)

(73) Assignee: Hainan Deze Drug Research Co., Ltd., Haikou Hainan (CN)

( * ) Notice: Subject to any disclaimer, the term of this patent is extended or adjusted under 35 U.S.C. 154(b) by 0 days.

(21) Appl. No.: 12/382,247

(22) Filed: Mar. 11, 2009

(65) Prior Publication Data

US 2009/0176816 A1   Jul. 9, 2009

Related U.S. Application Data

(63) Continuation of application No. PCT/CN2007/002684, filed on Sep. 11, 2007.

(30) Foreign Application Priority Data

Sep. 12, 2006   (CN) .......................... 2006 1 0122125

(51) Int. Cl.
*A61K 31/70* (2006.01)
*A61K 31/44* (2006.01)

(52) U.S. Cl. ........................................ 514/23; 514/280

(58) Field of Classification Search ................... 514/23, 514/280
See application file for complete search history.

(56) References Cited

FOREIGN PATENT DOCUMENTS

| CN | 1903236 | 1/2007 |
|---|---|---|
| CN | 101066275 | 11/2007 |

OTHER PUBLICATIONS

Dai, Ronghua et al., "Measurement for chimonin and berberine in Pill for Nourishing Didney-Yin by reversed-phase HPLC", Sep. 2002, Journal of Shenyang Pharmaceutical University, vol. 19, No. 5, pp. 332-334.

Yang, Huaijin, et al., "Research for active components in Traditional Chinese Medicine for Diabetes", Feb. 2005, Chinese Journal of Information on TCM, Vo. 12, No. 2, pp. 92-93.

International Search Report for International Application No. PCT/CN2007/002684, mailed Dec. 13, 2007.

*Primary Examiner*—Raymond J Henley, III
(74) *Attorney, Agent, or Firm*—Staas & Halsey LLP

(57) ABSTRACT

A drug composition for treating type 2 diabetes and diabetic chronicity complications is disclosed. The composition is composed of mangiferin and berberine in a certain ratio. The composition has a preferable hypoglycemic and hypolipidemic effect compared with mangiferin and berberine which is used alone.

6 Claims, No Drawings

DRUG COMPOSITION FOR TREATING 2 TYPE DIABETES AND DIABETIC CHRONICITY COMPLICATIONS

CROSS REFERENCE TO RELATED APPLICATION

This application is a continuation application filed under 35 U.S.C. §111(a), claiming the benefit under 35 U.S.C. §120 and §365(c) of a PCT International Application Number PCT/CN2007/002684, filed Sep. 11, 2007, it being further noted that foreign priority benefit is based upon Chinese Patent Application 200610122125.7, filed Sep. 12, 2006 in the State Intellectual Property Office of P.R. China, the disclosures of which are thereby incorporated by reference.

FIELD OF THE INVENTION

This invention relates to a drug composition for treating type 2 diabetes and diabetic chronic complications, the composition is composed of mangiferin and berberine.

BACKGROUND OF THE INVENTION

In recent years, type 2 diabetes and its chronic complications have become a threat to human health as the "third killer". According to statistics, standardized prevalence rate of type 2 diabetes in China has rapidly increased from 0.9 percent in the early 1980's to the current 5.21 percent; and the standardized prevalence rate of impaired glucose tolerance is 4.76 percent. Long-term hyperglycemia associated with type 2 diabetes results in the damage of many tissues and organs, which in turn lead to a variety of diabetic chronic complications, such as coronary heart disease, atherosclerosis, cerebrovascular disease and other diabetic macrovascular diseases, diabetic nephropathy, diabetic retinopathy and other diabetic microangiopathy, diabetic neuropathy, diabetic foot, diabetic maculopathy, diabetic cataract, diabetic glaucoma, refractive changes, iris and ciliary body diseases.

At present, most of the oral hypoglycemic agents that are on the market are expensive or have some adverse reactions, which cause poor compliance of patients. The pathogenesis of the diabetic chronic complications is not entirely clear, and there is no ideal drug in the clinical treatment. Therefore research and development of drugs that are low cost, but show high efficiency and low toxicity that not only has hypoglycemic effect but also prevent and treat diabetic chronic complications will have important clinical significance and market value.

Mangiferin, a natural polyphenol is from Liliaceae plants such as *Anemarrhena asphodeloides* Bunge. etc., molecular weight: 422, structural formula: $C_{19}H_{18}O_{11}$, and its chemical structure is as follows:

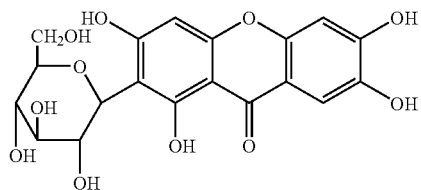

Mangiferin is a natural antioxidant. Pharmacological study shows that mangiferin has a variety of biological activity, such as anti-oxidation, anti-tumor, anti-bacterial, anti-virus, hypoglycemic, hypolipidemic effect, anti-inflammatory, choleretic, immunomodulation, etc. Mangiferin can lower blood glucose and lipid levels of diabetic rats or mice by oral or intraperitoneal injection. The potential mechanism of hypoglycemic is probably by increasing insulin sensitivity [Miura T, Ichiki H, Hashimoto I, et al. Antidiabetic activity of a xanthone compound, mangiferin, Phytomedicine, 2001, 8(2):85-87].

In recent years, more evidence show that the hyperglycemia, oxidative stress and diabetic chronic complications are closely related. Muruganandan's research shows that in the streptozotocin-induced diabetic rats, mangiferin by intraperitoneal injection can control the lipid peroxidation, and can reduce the glycosylated hemoglobin and serum creatine phosphate Kinase (CPK) of the diabetes rats and its complications due to chronic oxidative damage. Mangiferin can also protect animals avoiding the damage of heart and kidney. [Muruganandan S, Gupta S, Kataria M, et al. Mangiferin protects the streptozptocin-induced oxidative damage to cardiac and renal tissues in rats. Toxicology, 2002, 176(3):165-173]. The $LD_{50}$ of mangiferin by intraperitoneal injection once is 365 mg/kg in rat [Yu shengmin, Zhong ming. The research advance of pharmacology effects of the mangiferin. Chinese Journal of Traditional Medical Science and Technology, 1999, 6(3):199-200]. We can see that mangiferin is safe.

Because mangiferin cannot dissolve in water, there is limitation such as its bioavailability, and formulation.

Berberine (Ber) is an isoquinoline alkaloid that is extracted from the root and bark of *Coptis chinesis Franch* (Ranunculaceae coptis plant). Berberine is the main ingredient of the coptis. Molecular formula: $C_{20}H_{18}NO_4$, molecular weight: 336.37. Its chemical structure is as follows

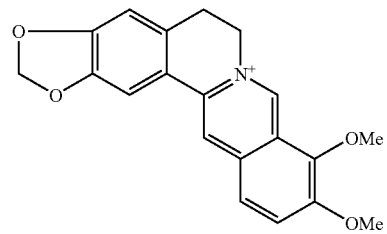

Pharmacological research of berberine shows that it has a variety of biological activities, such as anti-bacterial, anti-virus, hypoglycemic, anti-abnormal heart rate, lower blood pressure, anti-tumor, lipid-lowering, etc.

Animal experiments show that berberine can reduce the blood glucose of the normal mice, and the alloxan diabetic and chronic complications mice, and the spontaneous diabetic and chronic complications KK mice. The effect is significantly, the duration is long, while berberine can improve glucose tolerance of the KK mice. In recent years, clinical research has proven that berberine has the effects of anti-diabetes and improves its chronic complications, especially in the treatment of type 2 diabetes and chronic complications. The mechanism of the hypoglycemic effect may be by inhibiting the liver gluconeogenesis and/or promoting the glycolysis of the peripheral organizations, that is the non-insulin-dependent. But only under the conditions of moderately high glucose level (for example, 11.1 mmol/L), will berberine have significant hypoglycemic effect. However, under conditions of seriously high glucose level (for example, 22.2 mmol/L), the hypoglycemic effect of the berberine disappear. Berberine mainly applies to impaired glucose tolerance, abnormal fasting blood glucose and stable blood glucose of the diabetics [Yin jun, Hu renming, Chen mingdao, et al. Comparison of glucose consumption effects of Mmetformin, troglitazone and berberine on the HepG2 cells. Chinese Journal of Endocrinology and Metabolism, 2002, 18(6):488-489].

In recent years, studies have shown that sustained hyperglycemia can increase the activity of aldose reductase in cells which leads to diabetic neuropathy, diabetic retinopathy and a variety of vascular diseases. It is significant to inhibit aldose reductase activity on the treatment of chronic diabetic complications. Many scholars' studies showed that berberine can inhibit the activity of aldose reductase [Liu Changshan; Dong Yanhu; Pang Linan; et al. The effects of baicalin and berberine on proteinuria and glomerular ultrastructure in alloxan-induced diabetic rats. CHINESE JOURNAL OF DIABETES, 1996, 4(3):163].

Regarding the treatment dose, berberine is safe. Its side effects are few. We do not find any adverse reactions when berberine was used for long. we don't find any adverse reactions when berberine was taken 2.0 g once orally [Ji yubin. The effective composition and pharmacological action of Chinese medicine, Harbin: Heilongjiang Science and Technology Press, 2004, 77].

The bioavailability of berberine is very low. In a certain blood glucose range, berberine may play hypoglycemic role. As a result, the use of berberine in diabetic patients is limited significantly.

SUMMARY OF THE INVENTION

In order to develop low cost, highly effective and low toxic drug that not only have hypoglycemic effect but can also prevent and treat diabetic chronic complications. After a large number of studies, the inventor finds that the composition that is composed of mangiferin and berberine in a certain ratio have unexpected effect as follows:

First, the effect of a composition that is composed of mangiferin and berberine in the treatment of type 2 diabetes is significantly enhanced. Therefore, there are obvious synergies between mangiferin and berberine. It is as follows:

1. The composition has more prominent hypoglycemic effect, because non-insulin-dependent hypoglycemic effect of berberine combines with the insulin-sensitizing effect of mangiferin.

2, The composition is more effective to prevent and treat type 2 diabetic chronic complications, because the effect of antioxidant and lipid-lowering of the mangiferin combines with the effect of lipid-lowering and aldose reductase inhibition of the berberine.

Second, while mangiferin cannot dissolve in water alone, the dissolution of mangiferin is increased significantly in the composition of mangiferin and berberine.

Finally, the bioavailability of the mangiferin and berberine, when given alone, is low, but the bioavailability of mangiferin and berberine, when given as a composition, is improved significantly.

According to these beneficial effects of the composition, and high security of berberine and mangiferin single oral administration and low cost of raw materials of berberine and mangiferin, we can see the composition will be a low cost, highly effective, low toxic drug, which the drug not only has the hypoglycemic effect, but also prevents and treats diabetic chronic complications.

One aspect of the present invention is to provide a composition that can be prepared as a treatment of type 2 diabetes, having the following characteristics: the active ingredient of the composition is composed of mangiferin and berberine, the weight ratio range of mangiferin and berberine is 1:0.1 to 1:20.

The preferred weigh ratio range of mangiferin and berberine is 1:1 to 1:10.

The more preferred weigh ratio range of mangiferin and berberine is 1:3 to 1:6.

The composition as defined above, wherein: berberine can be berberine hydrochloride, berberine sulfate, tannin berberine or other medically acceptable salt of berberine.

Still another aspect of the present invention is to provide the use of the composition as defined above, as a treatment of type 2 diabetes.

The treatment of type 2 diabetes as defined above can also be used as a hypoglycemic agent.

The treatment drug of type 2 diabetes as defined above can also be used as a drug to prevent and treat type 2 diabetes and diabetic chronic complications.

Diabetic chronic complications refers to one or more of diabetic macrovascular diseases, diabetic microangiopathy, diabetic neuropathy, diabetic foot, diabetic maculopathy, diabetic cataract, diabetic glaucoma, refractive changes, iris and ciliary body diseases.

Yet another aspect of the present invention is to provide a drug, such that the drug is composed of the composition as defined above with a pharmaceutical acceptable auxiliary material. The drug may be in the form of oral formulations, such as tablets, capsules, gentle capsules, granules, pills, syrup, oral solution, oral suspension, etc.

Furthermore, another aspect of the present invention is to provide an effective dose range of the composition as defined above. For in stance, in rats, the effective dose range is about 20 to 350 mg/day. Based on the effective dose ranges of different types of animals, conversion formula imply that the effective dose range will be about 200 to 3500 mg/day/person by oral administration three times or four times per day. Because of the difference between animals and the human body, the adjustments of the dose and times in actual clinical application can be allowed.

Embodiments of the invention may be explained in detail in the following examples given below. These examples are provided as further illustrations of the invention, and therefore should not be construed to limit the scope of the invention.

EXAMPLES

Berberine, berberine hydrochloride, berberine sulfate, tannin berberine, and mangiferin in the invention can be purchased from market sources, for example at the price of about RMB 1000 yuan/kg. They can also be obtained by conventional extraction methods, such as those described here.

Example 1

Preparation of Berberine

Berberine hydrochloride (more than 98% purity) is dissolved in hot water. After the pH of the solution is adjusted to 10-12 with ammonia, the reaction solution is set aside for more than 12 hours. Then the reaction solution is filtrated, and the deposition is dried, the deposition is berberine. The purity of berberine is determined to be 98.5% by HPLC.

Example 2

Preparation of Mangiferin

Rhizoma anemarrhenae is extracted with 75% aqueous ethanol for one hour twice. The extracts are concentrated. The evaporated extract is adsorbed by macroporous resin, and then the macroporous resin is eluted with water adequately. Then the macroporous resin is eluted with 20% aqueous ethanol, the solution is concentrated to obtain crude nemangiferin. Then the macroporous resin is eluted with 40% aqueous ethanol, the solution is concentrated to obtain crude mangiferin. The crude mangiferin and nemangiferin are recrystallized. The pure mangiferin and nemangiferin are obtained, their purity is determined to be more than 95% by HPLC.

Example 3

Preparation of Mangiferin Tablets

The formulation containing: mangiferin 100 g, microcrystalline cellulose 100 g, and starch 100 g is used to prepare 1000 tablets.

Mangiferin, starch and microcrystalline cellulose are mixed uniformly. An appropriate bond is added into the drug mixture in order to crank out granule. The granule is dried and then pressed by tablet press machine. 1000 tablets are prepared. The tablets are coated with a film. There are 100 mg mangiferin in every tablet.

Example 4

Preparation of Mangiferin-Berberine Tablets

The formulation containing: mangiferin 90.9 g, berberine 9.1 g, carboxymethyl cellulose 80 g, and pregelatinized starch 120 g is used to prepare 1000 tablets.

Mangiferin and berberine are mixed uniformly, then the drug mixture, carboxymethyl cellulose and pregelatinized starch are mixed uniformly. An appropriate bond is added into the drug mixture in order to crank out granule. The granule is dried and then pressed by tablet press machine. 1000 tablets are prepared. The tablets are coated with a film.

Example 5

Preparation of Mangiferin-Berberine Tablets

The formulation containing: mangiferin 50 g, berberine 50 g, microcrystalline cellulose 60 g, and pregelatinized starch 140 g is used to prepare 1000 tablets.

Mangiferin and berberine are mixed uniformly, then the drug mixture, microcrystalline cellulose and pregelatinized starch are mixed uniformly. An appropriate bond is added into the drug mixture in order to crank out granule. The granule is dried and then pressed by tablet press machine. 1000 tablets are prepared. The tablets are coated with a film.

Example 6

Preparation of Mangiferin-Berberine Tablets

The formulation containing: mangiferin 25 g, berberine 75 g, microcrystalline cellulose 40 g and pregelatinized starch 160 is used to prepare 1000 tablets.

Mangiferin and berberine are mixed uniformly, then the drug mixture, microcrystalline cellulose and pregelatinized starch are mixed uniformly. An appropriate bond is added into the drug mixture in order to crank out granule. The granule is dried and then pressed by tablet press machine. 1000 tablets are prepared. The tablets are coated with a film.

Example 7

Preparation of Mangiferin-Berberine Tablets

The formulation containing: mangiferin 14 g, berberine 86 g, microcrystalline cellulose 60 g and pregelatinized starch 140 g is used to prepare 1000 tablets.

Mangiferin and berberine are mixed uniformly, then the drug mixture, microcrystalline cellulose and pregelatinized starch are mixed uniformly. An appropriate bond is added into the drug mixture in order to crank out granule. The granule is dried and then pressed by tablet press machine. 1000 tablets are prepared. The tablets are coated with a film.

Example 8

Preparation of Mangiferin-Berberine Tablets

The formulation containing: mangiferin 9 g, berberine 91 g, microcrystalline cellulose 30 g, and starch 170 g is used to prepare 1000 tablets.

Mangiferin and berberine are mixed uniformly, then the drug mixture, microcrystalline cellulose and starch are mixed uniformly. Appropriate bond is added into the drug mixture in order to crank out granule. The granule is dried and then pressed by tablet press machine. 1000 tablets are prepared. The tablets are coated with a film.

Example 9

Preparation of Mangiferin-Berberine Tablets

The formulation containing: mangiferin 4.8 g, berberine 95.2 g, microcrystalline cellulose 40 g, and pregelatinized starch 160 g is used to prepare 1000 tablets.

Mangiferin and berberine are mixed uniformly, then the drug mixture, microcrystalline cellulose and pregelatinized starch are mixed uniformly. Appropriate bond is added into the drug mixture in order to crank out granule. The granule is dried and then pressed by tablet press machine. 1000 tablets are prepared. The tablets are coated with a film.

Example 10

Preparation of Berberine Tablets

The formulation containing: berberine 100 g, and an appropriate starch is used to prepare 1000 tablets.

Berberine and starch are mixed uniformly. An appropriate bond is added into the drug mixture in order to crank out granule. The granule is dried and then pressed by tablet press machine. 1000 tablets are prepared. The tablets are coated with a film. There is 100 mg berberine in every tablet.

Example 11

Preparation of Mangiferin-Berberine Hydrochloride Tablets

The formulation containing: mangiferin 25 g, berberine hydrochloride 75 g, methylcellulose 20 g and pregelatinized starch 180 g is used to prepare 1000 tablets.

Mangiferin and berberine hydrochloride are mixed uniformly, then the drug mixture, methylcellulose and pregelatinized starch are mixed uniformly. An appropriate bond is added into the drug mixture in order to crank out granule. The granule is dried and then pressed by tablet press machine. 1000 tablets are prepared. The tablets are coated with a film.

Example 12

Preparation of Mangiferin-Berberine Tannate Granules

The formulation containing: mangiferin 28 g, berberine tannate 172 g, sucrose 600 g and carboxymethyl cellulose 200 g is used to prepare 1000 granules.

Mangiferin and berberine tannate are mixed uniformly, then the drug mixture, sucrose and carboxy methyl cellulose are mixed uniformly. An appropriate bond is added into the drug mixture in order to crank out granule. The granules is dried and packed.

Example 13

Preparation of Mangiferin-Berberine Hydrochloride Capsule

The formulation containing: mangiferin 14.3 g, berberine hydrochloride 85.7 g, microcrystalline cellulose 20 g and pregelatinized starch 80 g is used to prepare 1000 capsules.

Mangiferin and berberine hydrochloride are mixed uniformly, then the drug mixture, microcrystalline cellulose and pregelatinized starch are mixed uniformly. An appropriate bond is added into the drug mixture in order to crank out granule. The granule is dried and then capsules are filled 0.1000 capsules are prepared.

Example 14

Preparation of Mangiferin-Berberine Pills

The formulation containing: mangiferin 20 g, berberine 80 g, and macrogol 4000 400 g is used.

Mangiferin and berberine are mixed uniformly, the macrogol 4000 is smelt in hot water. Then the drug mixture is mixed uniformly at 75° C., the drug suspension is transferred into storage cans of pill machine at 75° C.

The technology parameter of pills: caliber: 30/4.0 mm; dropping speed: 60 dripping/min; refrigerant: dimethyl silicone oil; the temperature of refrigerant: 20° C.±2° C.; pill weight: 40 mg.

The residue refrigerant on pills surface is removed, then the pills are packed.

Dissolution Rate of the Composition of Mangiferin and Berberine

Six tablets samples were taken from each of example 3, example, 6 and example, 10. The tablet samples of examples 3 were designated as MAG, the tablet samples of examples 6 were designated as MB, the tablet samples of examples 10 are designated as BER. The experiment was performed in rotating basket method according to the addenda of China Pharmacopoeia. The samples were put into phosphate buffer solution (PBS, 900 ml, pH 6.8). The rotating speed was 100 r/min. 2 ml solution of samples were taken out separately at 5 min, 10 min, 20 min, 30 min, 60 min, 120 min, 240 min, 360 min, and 480 min. The same volume of PBS was supplied at once. The samples solutions were filtrated with microporous filtration membrane which specification is 0.45 μm.

The concentration of mangiferin and berberine were determined, the dissolution rate was accounted. The result is as table 1.

Conclusion: the dissolution rate of the composition of mangiferin and berberine is significantly improved when compared with formulation containing only mangiferin.

The Pharmacokinetics of the Composition after Oral Administration

1. The Confect of Drug Solution

Mangiferin is suspended in 1% carboxymethyl cellulose sodium solution, the concentration of mangiferin is 25 mg/mL (Sample A).

Berberine is suspended in 1% carboxymethyl cellulose sodium solution, the concentration of berberine is 25 mg/mL (Sample B). The composition which is composed of mangiferin and berberine in the ratio of 1:4 is suspended in 1% carboxymethyl cellulose sodium solution, the concentration of the composition is 50 mg/mL (Sample C).

2. Oral Administrated Project

All rats were fasted for 16 hours and drunk water freely. The rats are oral administrated respectively sample A (40 mg/kg), sample B (160 mg/kg) and sample C (200 mg/kg). From the rats, 0.4 ml blood samples were taken respectively at the time of 5 minutes before oral administrated and 0 h, 1 h, 2 h, 3 h, 4 h, 5 h, 6 h, 8 h, 10 h, 12 h, 15 h, and 24 h after oral administrated. These blood samples were put into centrifuge tube containing heparin, then were centrifuged for 10 minutes, the serum is obtained.

3. Serum Sample Treatment

Serum samples are taken accurately 100 μL into centrifuge tubes, then 400 μL acetonitrile-acetic acid (9:1) is added into centrifuge tubes. The samples are whorled for 1.5 minutes, and then the samples are centrifuged 3000 r/min for 10 minutes. The supernatant was put into clear tube, dried by nitrogen, 100 μL mobile phase were put into the remnants, whorled for 1.5 minutes, then centrifuged 3000 r/min for 10 minutes. The Supernatant was put into sample bottle. All the samples are determined by HPLC. Injection volume is 20 μL.

4. The Analysis of the Samples 4.1 Apparatus: Angilent 1100 HPLC (American Agilent Co.): include G1312A dual pump and G1313A Auto-Sampler.

4.2 Chromatographic Conditions:

Chromatographic column: discover ODS column (250 mm×6 mm, 5 μm);

The mobile phase: methanol-0.1% $H_3PO4$ water.

Velocity of flow: 1.0 ml/min.

Detection Wavelength: 264 nm.

Column temperature: 40□

TABLE 1 the dissolution rate of the composition of mangiferin and berberine

| Sample | The component of dissolution | Average dissolution rate (%) at different time (min) (n = 6) | | | | | | | | |
|---|---|---|---|---|---|---|---|---|---|---|
| | | 5 | 10 | 20 | 30 | 60 | 120 | 240 | 360 | 480 |
| MAG | mangiferin | 8.62 | 11.69 | 16.62 | 21.69 | 26.13 | 30.73 | 36.24 | 38.55 | 41.14 |
| MB | mangiferin | 21.99 | 37.03 | 48.54 | 73.61 | 84.67 | 90.14 | 92.28 | 95.46 | 96.58 |
| | berberine | 30.26 | 42.77 | 55.61 | 72.88 | 86.37 | 90.87 | 93.03 | 96.43 | 97.24 |
| BER | berberine | 31.18 | 43.93 | 56.11 | 74.62 | 87.71 | 91.16 | 94.64 | 96.36 | 97.37 |

TABLE 2 the Pharmacokinetics of the composition after oral administration

| parameter | mangiferin | berberine | The composition | |
|---|---|---|---|---|
| Cmax (μg/ml) | 18.6 ± 1.5 | 54.1 ± 2.6 | mangiferin | 34.2 ± 2.6 |
| | | | berberine | 87.4 ± 3.1 |
| $T_{1/2}\beta$ (hr) | 4.3 ± 0.4 | 3.5 ± 0.3 | mangiferin | 6.2 ± 0.5 |
| | | | berberine | 4.4 ± 0.4 |
| $AUC_{0-\infty}$/ μg · h/ml | 1198.6 ± 390.7 | 3439.5 ± 249.8 | mangiferin | 2158.5 ± 215.6 |
| | | | berberine | 4641.5 ± 380.4 |

5. Results:

According to the data (Table 2), the pharmacokinetics data of the composition that is composed of mangiferin and berberine is better than mangiferin or berberine orally alone. The $C_{max}$, and AUC of mangiferin and berberine of the composition is better than mangiferin or berberine orally alone. It suggests that there is interaction in promoting absorption between mangiferin and berberine.

In the following experiments, kidney and lens are the representative organs of diabetic chronic complications.

The GK (Goto-Kakizaki) rat is the spontaneous model of diabetes, the pathogenesis of GK rat is very similar to the pathogenesis of type 2 diabetes. After diabetes attack, hyperglycemia and insulin secretion weakened emerge rapidly, the latter diseases may be complicated by retinopathy, microvascular disease, neuropathy, nephropathy in GK rat. The GK rats have been widely used in type 2 diabetes study, so we choose GK rat as the animal model of the following experiment.

The Effect of the Mangiferin, Berberine and Compositions in GK Rats

1. Materials 1.1 Mangiferin and berberine are prepared in accordance with the method of preparation of example 1 and 2. Then they can be mixed or diluted in accordance with the dose and the ratio.

1.2 NADPH, NADH: Sigma's products; DL-glyceraldehyde: Italy Roth products.

1.3 Goto-Kakizaki rats (GK) (4 months age, ♀♂) and Wistar rats (SPF level, ♀♂) were purchased from Shanghai SLAC laboratory animal Co., Ltd.

In addition to the normal rats, the other rats were fed with high fat diet (20% protein and 3.5% cholesterol).

2. Experimental Group:

After the rats was feeding adaptation for one week, The GK rats which the blood glucose level was more than 11.1 mmol/L were selected, and then divided into the following groups random:

GK rats control group (n=10); mangiferin groups (10, 30, 200 mg/kg, each group 10 rats); berberine groups (10, 20, 150 mg/kg, each group 10 rats); composition group 1[[mangiferin (10 mg/kg)+berberine (10 mg/kg)], 10 rats]; composition group 2[[mangiferin (200 mg/kg)+berberine (150 mg/kg)], 10 rats]. Wistar rats are normal control group (10 rats). GK rats control group and Wistar rats group were given saline. The other groups were given test drugs. Test samples were administrated orally at the same time every day for 12 weeks.

3. Measurements:

3.1 Blood Glucose and lipid: The blood specimens were taken at the end of the test. Plasma glucose (GLU), triglycerides (TG), total cholesterol (TC) were determined by HITACHI7080 automatic biochemistry analyzer.

3.2 The activity of aldose reductase (AR): At the End of the experiment, the left side lens of rats was taken, then these lenses were added into glycerol and put into refrigerator (−80° C.☐) to preserve to determine AR activity. The determination method of AR activity refer to Maragoudakis's method and change slightly, that is: the activity of enzyme is indicated by the record of the absorbance of NADPH in 340 nm decline IOU. This study used two reaction systems, the first reaction system includes $Na^+$—$K^+$ Phosphate Buffered Saline (67 mmol/L, pH6.2), DL-glyceraldehyde (10 mmol/L), 2-mercaptoethanol (5 mmol/L), L), NADPH (0.1 mmol/L), and appropriate quantity enzyme; experimental cup includes all reagents, in the control cup double distilled water take the place of DL-glyceraldehyde. The second reaction system is 0.1 mmol/L NADH instead of NADPH, the rest of the reagent is same as one of the first response system. The activity of enzyme and the protein content in tissue homogenate are determined at the same time. a unit enzyme activity is indicated by the quantity of the enzyme that produce 1 μmol $NADP^+$ (or $NDA^+$) in one minute. The enzyme activity of the organizations is showed with specific activity, the specific activity equal enzyme units/mg protein.

3.3 Measurements about Oxidation 3.3.1 Preparation of tissue homogenate: Rats were killed by femoral artery bloodletting after administration of the rats for 12-weeks. Kidney tissue of the rats were taken, the blood of kidney tissue were washed with cooling saline (4° C.), then the remnant water was absorbed with filter paper, the kidney tissue was weighed. Per gram kidney tissue was added into 10 ml saline, which was put in homogenized machine (10,000 r/min, 10 seconds, 3rd), 10% tissue homogenate was prepared, the tissue homogenate was centrifuged (4000 r/min) for 10 minutes to get supernatant, the supernatant was saved in −20° C. for determination.

3.3.2 Determination of the Measurements about Oxidation 3.3.2.1 Superoxidedismutase (SOD): SOD is determined by Xanthine Oxidase calorimetric analysis, the test box was bought from Nanjing Jiancheng Bioengineering Research Institute.

3.3.2.2 Propyl dialdehyde (MDA): MDA is determined by TBA, the test box was bought from Nanjing Jiancheng Bioengineering Research Institute.

3.4 Statistics: The results have been calculated as mean±SD ($\bar{x}$±SD) and the comparisons of the data have been done by t-test.

4. Results 10 mg/kg mangiferin and 10 mg/kg berberine do not significantly improve GLU, TC, TG, AR, MDA, SOD in diabetic GK rats. 30 mg/kg mangiferin and 20 mg/kg berberine improves GLU, TC, TG, AR, MDA, SOD in diabetic GK rats.

The composition [mangiferin (10 mg/kg)+berberine (10 mg/kg)] significantly improves GLU, TC, TG, AR, MDA, SOD in diabetic GK rats (p<0.01, compared with GK rats control group). There is significant differences between the composition group with 30 mg/kg mangiferin group and 20 mg/kg berberine group (p<0.05). There are obvious synergies between mangiferin and berberine.

The composition [mangiferin (200 mg/kg)+berberine (150 mg/kg)] significantly improves GLU, C, TG, AR, MDA, SOD in diabetic GK rats (p<0.001, compared with GK rats control group) (Table 4).

5. Conclusions

These results suggest that the composition that is composed of mangiferin and berberine has preferable hypoglycemic effect compared with mangiferin and berberine which is used alone.

Because the composition has the hypolipidemic effect and improving the oxidation measurements of kidney and the AR activity of lens, the composition has the effect of prevention and treatment of chronic diabetic complications.

The Effect of the Different Ratio Compositions in GK Rats

1. Material 1.1 Sample: Mangiferin and berberine are prepared in accordance with the method of preparation of example 1 and 2. Then they can be mixed in accordance with the dose and the ratio such as table 3.

1.2 Animal: Goto-Kakizaki rats (GK) (4 months age, ♀♂) and Wistar rats (SPF level, ♀♂) were purchased from Shanghai SLAC laboratory animal Co., Ltd.

In addition to the normal rats, the other rats were fed with high fat diet (20% protein and 3.5% cholesterol).

2. Experimental Group:

After the rats was feeding adaptation for one week, GK rats that the blood glucose level of the GK rats was more than 11.1 mmol/L were selected, and then random divided into the following groups as follows (Table 3):

There are ten rats in every group. GK rats control group and wistar rats group were given saline. The other groups were given test drugs. Test samples were administrated orally at the same time every day for 12 weeks.

TABLE 3

| | the ratio of the composition | | |
|---|---|---|---|
| | mangiferin (mg/kg) | berberine (mg/kg) | mangiferin:berberine |
| Composition A | 20 | 0 | |
| Composition B | 18.2 | 1.8 | 1:0.1 |
| Composition C | 10 | 10 | 1:1 |
| Composition D | 5 | 15 | 1:3 |
| Composition E | 2.8 | 17.2 | 1:6 |
| Composition F | 1.8 | 18.2 | 1:10 |
| Composition G | 0.95 | 19.05 | 1:20 |
| Composition H | 0 | 20 | |

3. Measurements:

The measurements are as same as the above experiment.

4. Results

The results as shown in table 5, the different ratio compositions have significantly improved GLU, TC, TG, AR, MDA, SOD in diabetic GK rats.

TABLE 4 the effect of the mangiferin, berberine and compositions in GK rats

| Groups | n | GLU (mmol/L) | Lipid | | AR activity of lens |
|---|---|---|---|---|---|
| | | | TG (mmol/L) | TC (mmol/L) | NADPH (0.1 mmol/L) |
| Normal control group | 10 | 6.45 ± 0.37** | 1.40 ± 0.15** | 1.25 ± 0.13** | 0.56 ± 0.35** |
| GK rats control group | 10 | 20.63 ± 3.24 | 3.51 ± 0.37 | 4.50 ± 1.36 | 5.40 ± 2.15 |
| Mangiferin group (10 mg/kg) | 10 | 20.75 ± 3.39 | 3.62 ± 0.41 | 4.48 ± 1.53 | 5.36 ± 2.17 |
| Mangiferin group (30 mg/kg) | 10 | 13.05 ± 2.23* | 2.82 ± 0.22* | 3.16 ± 0.32* | 3.05 ± 0.59* |
| Mangiferin group (200 mg/kg) | 10 | 9.05 ± 2.04** | 1.82 ± 0.32* | 3.06 ± 0.29* | 1.87 ± 0.51** |
| Berberine group (10 mg/kg) | 10 | 21.24 ± 3.13 | 3.49 ± 0.68 | 4.53 ± 1.28 | 5.64 ± 2.19 |
| Berberine group (20 mg/kg) | 10 | 12.29 ± 2.76* | 2.79 ± 0.24* | 3.27 ± 0.24* | 2.28 ± 0.51* |
| Berberine group (150 mg/kg) | 10 | 9.11 ± 2.08** | 1.80 ± 0.19* | 3.01 ± 0.28* | 1.87 ± 0.51** |
| Composition group 1 | 10 | 8.35 ± 2.09**˅# | 1.87 ± 0.56**˅# | 2.96 ± 0.46**˅# | 1.74 ± 0.47**˅# |
| Composition group 2 | 10 | 6.11 ± 2.02*** | 1.51 ± 0.20*** | 1.37 ± 0.29*** | 1.60 ± 0.55*** |

| Groups | AR activity of lens | Measurements about oxidation | |
|---|---|---|---|
| | NADH (0.1 mmol/L) | SOD (U/mg pro) | MDA (nmol/mg pro) |
| Normal control group | 0.30 ± 0.15** | 210.43 ± 30.32** | 2.59 ± 0.58** |
| GK rats control group | 2.90 ± 0.75 | 132.56 ± 23.50 | 4.37 ± 0.92 |
| Mangiferin group (10 mg/kg) | 2.89 ± 0.69 | 130.74 ± 23.47 | 4.41 ± 0.87 |
| Mangiferin group (30 mg/kg) | 1.64 ± 0.42* | 168.23 ± 13.46* | 3.48 ± 0.47* |
| Mangiferin group (200 mg/kg) | 0.94 ± 0.45** | 194.15 ± 13.55** | 2.75 ± 0.48** |
| Berberine group (10 mg/kg) | 2.98 ± 0.60 | 131.56 ± 23.49 | 4.39 ± 0.90 |
| Berberine group (20 mg/kg) | 1.32 ± 0.37* | 170.04 ± 13.49* | 3.51 ± 0.46* |
| Berberine group (150 mg/kg) | 0.94 ± 0.45** | 195.10 ± 13.71** | 2.76 ± 0.40** |
| Composition group 1 | 0.91 ± 0.15**˅# | 200.51 ± 33.25**˅# | 2.03 ± 0.41**˅# |
| Composition group 2 | 0.65 ± 0.11*** | 218.51 ± 33.15*** | 2.57 ± 0.33*** |

Table 4:
compared with GK rats control group:
*p < 0.05,

TABLE 4-continued the effect of the mangiferin, berberine and compositions in GK rats \*\*p < 0.01,
\*\*\*p < 0.001;
compared with mangiferin 30 mg/kg group:
ˇp < 0.05,
˘p < 0.01;
compared with berberine 20 mg/kg group:
p < 0.05,
p < 0.01.

TABLE 5 the effect of the different ratio compositions in GK rats

| Groups | GLU (mmol/L) | Lipid | | AR activity of lens |
| --- | --- | --- | --- | --- |
| | | TG (mmol/L) | TC (mmol/L) | NADPH (0.1 mmol/L) |
| Normal control group | 6.23 ± 0.29\*\* | 1.39 ± 0.15\*\* | 1.15 ± 0.16\*\* | 0.65 ± 0.41\*\* |
| GK rats control group | 21.45 ± 3.25 | 3.56 ± 0.38 | 4.62 ± 1.36 | 5.68 ± 2.23 |
| Composition A | 14.11 ± 2.03\* | 2.79 ± 0.30\* | 3.26 ± 0.26\* | 3.11 ± 0.56\*\* |
| Composition B | 10.25 ± 2.31\*\*ˇ# | 1.91 ± 0.02\*\*ˇ# | 3.17 ± 0.22\*ˇ# | 2.81 ± 0.61\*\*ˇ# |
| Composition C | 9.27 ± 2.06\*\*ˇ## | 1.92 ± 0.24\*\*ˇ# | 3.07 ± 0.28\*ˇ# | 1.79 ± 0.59\*\*ˇ# |
| Composition D | 6.47 ± 2.08\*\*ˇ## | 1.67 ± 0.55\*\*ˇ# | 2.68 ± 0.38\*\*ˇ# | 1.44 ± 0.49\*\*ˇ# |
| Composition E | 6.30 ± 2.09\*\*ˇ## | 1.48 ± 0.21\*\*ˇ# | 1.48 ± 0.28\*\*ˇ# | 1.58 ± 0.56\*\*ˇ# |
| Composition F | 9.29 ± 2.09\*\*ˇ## | 1.79 ± 0.21\*\*ˇ# | 3.19 ± 0.28\*ˇ# | 1.99 ± 0.54\*\*ˇ# |
| Composition G | 10.95 ± 3.23\*\*ˇ# | 1.90 ± 0.34\*\*ˇ# | 3.24 ± 0.56\*ˇ# | 2.28 ± 0.51\*\*ˇ# |
| Composition H | 12.34 ± 2.09\* | 2.91 ± 0.09\* | 3.33 ± 0.26\* | 2.48 ± 0.58\*\* |

| Groups | AR activity of lens | Measurements about oxidation | |
| --- | --- | --- | --- |
| | NADH (0.1 mmol/L) | SOD (U/mg pro) | MDA (nmol/mg pro) |
| Normal control group | 0.29 ± 0.15\*\* | 220.56 ± 30.33\*\* | 2.56 ± 0.54\*\* |
| GK rats control group | 2.99 ± 0.65 | 135.57 ± 23.06 | 4.33 ± 0.90 |
| Composition A | 1.97 ± 0.46\*\* | 168.26 ± 13.50\*\* | 3.43 ± 0.89\* |
| Composition B | 1.64 ± 0.45\*ˇ# | 178.23 ± 13.63\*ˇ# | 2.97 ± 0.40\*\*ˇ# |
| Composition C | 0.99 ± 0.41\*\*ˇ# | 195.17 ± 13.47\*\*ˇ# | 2.87 ± 0.46\*\*ˇ# |
| Composition D | 0.71 ± 0.14\*\*ˇ# | 208.14 ± 33.05\*\*ˇ## | 2.61 ± 0.45\*\*ˇ# |
| Composition E | 0.58 ± 0.21\*\*ˇ# | 218.59 ± 32.16\*\*ˇ## | 2.67 ± 0.44\*\*ˇ# |
| Composition F | 0.97 ± 0.66\*ˇ# | 195.67 ± 13.70\*ˇ# | 2.89 ± 0.42\*\*ˇ# |
| Composition G | 0.68 ± 0.42\*ˇ# | 179.14 ± 13.47\*ˇ# | 2.92 ± 0.41\*\*ˇ# |
| Composition H | 1.39 ± 0.53\* | 171.10 ± 13.81\* | 3.52 ± 0.77\* |

Table 5:
compared with the GK rats control group:
\*p < 0.05,
\*\*p < 0.01,
\*\*\*p < 0.001;
compared with compositon A:
ˇp < 0.05,
˘p < 0.01;
compared with compositon H:
p < 0.05,
p < 0.01.

I claim:

1. A composition for treating type 2 diabetes, the composition comprising mangiferin and berberine, wherein the weight ratio range of mangiferin and berberine is 1:0.1 to 1:20.

2. The composition according to claim 1, wherein the weight ratio range of mangiferin and berberine is 1:1 to 1:10.

3. The composition according to claim 2, wherein: the weight ratio range of mangiferin and berberine is 1:3 to 1:6.

4. The composition according to claim 1, wherein: berberine is berberine hydrochloride, berberine sulfate, tannin berberine or a medically acceptable salt of berberine.

5. A drug for treating type 2 diabetes, wherein the drug comprises an effective amount of the composition as claimed in claim 1, and a pharmaceutically acceptable auxiliary material.

6. The drug according to claim 5, wherein the drug is an oral formulation in the form of a tablet, a capsule, a gentle capsule, a granule, a pill, a syrup, an oral solution, or an oral suspension.

\* \* \* \* \*